United States Patent [19]

Johansson et al.

[11] 4,445,506
[45] May 1, 1984

[54] BONE ALIGNING APPARATUS

[75] Inventors: Kjell Johansson; Hermino Duarte-Martins, Jr., both of Sundsvall, Sweden

[73] Assignee: Landstingens Inkopscentral, LIC, Solna, Sweden

[21] Appl. No.: 377,954

[22] Filed: May 13, 1982

[30] Foreign Application Priority Data

May 13, 1981 [SE] Sweden ................................. 8103017

[51] Int. Cl.³ ............................................... A61F 5/04
[52] U.S. Cl. ................................................. 128/84 R
[58] Field of Search ................ 128/84 B, 84 C, 84 R, 128/84 A, 83, 82, 75, 77, 78

[56] References Cited

U.S. PATENT DOCUMENTS

| 2,243,294 | 5/1941 | Stearns | 128/84 R |
| 3,105,489 | 10/1963 | Zivi | 128/84 R X |
| 3,850,166 | 11/1974 | Tammy et al. | 128/84 C |
| 3,871,366 | 3/1975 | Cotrel | 128/84 C X |

FOREIGN PATENT DOCUMENTS

| 363452 | 10/1938 | Italy | 128/84 R |
| 308753 | 9/1971 | U.S.S.R. | 128/84 C |

Primary Examiner—Ronald L. Frinks
Attorney, Agent, or Firm—Witherspoon & Hargest

[57] ABSTRACT

The present invention briefly refers to a bone aligning apparatus comprising a stand (1, 4, 7) forming a stretching bow in which a limb, preferably a fore arm, is insertable in order to be exposed to a repositioning pulling force. A rope (11) extends between a pulling force producing device (10) and a repositioning disc (15) having means (16) for holding the extreme portions of the limb such as fingers and toes in a physiologically correct position. A holding cuff (14) is adapted to retain the inner portion of the limb such as the upper arm or thigh, such cuff being attached to a portion (7) of the stand by means of a spring (13). A pulling force meter (18) is provided to establish the pulling force.

6 Claims, 1 Drawing Figure

U.S. Patent
May 1, 1984
4,445,506
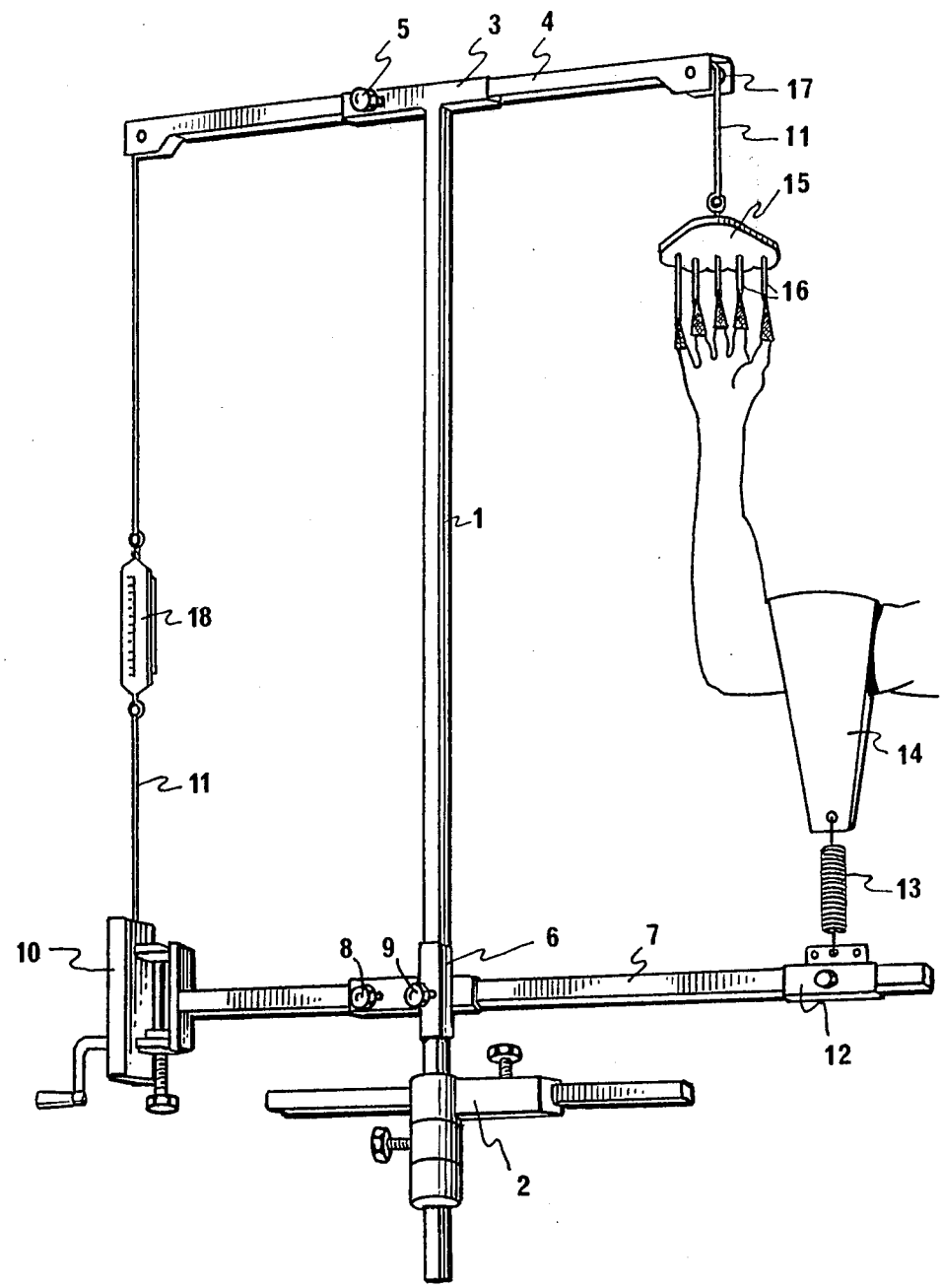

BONE ALIGNING APPARATUS

The present invention relates to a bone aligning apparatus, in particular an apparatus for the repositioning of bones in fore arms.

Reposition is performed in order to put broken bones in limbs into correct position prior to the application of a plaster-of-Paris bandage. The ordinary procedure involves the assistance of several persons pulling, turning and holding the damaged limb in such a way that the bones occupy the correct position when the plastering is performed. Such a procedure always requires the aid of several persons and may be extremely painful to the damaged person. In many cases it may also be difficult and sometimes completely impossible to perform X-ray photo-graphing during the repositioning work in order to find out whether the bones are in correct position prior to applying the plaster-of-Paris bandage.

It is the purpose of the present invention to eliminate the above-mentioned problems. This purpose is achieved by means of an apparatus of the type defind in the claims and having the specific characteristic features mentioned there.

The invention will be described in detail hereafter by reference to the attached drawing being a perspective view of the repositioning apparatus according to the invention during use.

The embodiment shown in the drawing of the repositioning apparatus according to the invention is predominantly composed of four-edged tubing comprising a vertical stand 1 which at its lower end is provided with attaching means 2 for attachment to an operating table, a particular holder or the like and which at its upper end has a cross piece 3. Also the cross piece 3 is constituted by four-edged tubing and slidingly receives upper beam 4 which by means of a latching knob 5 may be latched in various positions of adjustment.

A cross piece 6 is shiftable on the lower end of stand 1 and a lower beam 7 extends shiftably through the cross piece 6. With the aid of latching knobs 8, 9 the lower beam 7 may be latched in various positions both longitudinally and vertically.

At the one end the lower beam 7 is provided with a crank device 10 adapted to tension rope 11. This crank device 10 is swingably mounted at the end of lower beam 7.

A holder 12 is shiftably and latchably supported on the other end of the lower beam 7. By means of a spring 13 an upper arm cuff 14 is connected to holder 12.

Rope 11 extends from crank device 10 up to the upper beam 4 and through this beam to a repositioning disc 15 having finger holders 16. Rollers 17 are inserted in either end of the upper beam 4 to support rope 11. A force meter 18 subdivides the rope 11 extending between the crank device 10 and the upper beam 4.

When the repositioning apparatus according to the invention is used, the damaged arm is positioned as shown in the drawing. The adjustment of the apparatus should be such as to give the patient a comfortable position, for example sitting on a chair laterally of the apparatus. Thus repositioning disc 15 is so shaped that the fingers are held apart in a physiologically correct position and the finger holders 16 hold the fingers so that the arm may be subjected to a pulling force.

After adjustment of correct position a pulling force is applied to rope 11 with the aid of crank device 10, the magnitude of the pulling force being readable on the force mater 18. Normally the pulling force should amount to about 10 percent of the weight of the patient.

During this extension of the damaged fore arm the bones slowly but securily will be moved into correct position. Due to the fact that the pulling force is even and not particularly strong, the repositioning is less painful to the patient in comparison to the prior-art practice in which several persons manually try to bring about the same result. By using the present apparatus it is also easy to perform X-ray photographing of the damaged place to find out the correct time for the application of the plaster-or-Paris bandage, normally requiring between 15 and 20 minutes after the application of the repositioning pulling force to the damaged arm.

Obviously, the apparatus according to the invention can easily be adjusted for use in the repositioning of limbs other than fore arms, it is being particularly simple to readjust the apparatus for repositioning fore legs.

The essential portions of the apparatus according to the invention are, on the one hand, the repositioning disc 15 fixing the fingers in the physiologically correct position and, on the other hand, the stretching bow performing the dynamic pulling-lifting force in the fore arm. Due to this fundamental constructive idea the muscles are caused to relax which facilitates repositioning while at the same time the wrist and fore arm are easily accessible for manipulation and reduction of the luxation forces by the fracture. There are not either any constructive details obstructing the performance of X-ray and plastering operations.

The apparatus as shown is extremely flexible, on the one hand, due to its universal attachment permitting many possibilities of attachment and, on the other hand, due to the adjustability laterally and vertically. Due to the fact that the apparatus is constructed of four-edged tubing the construction will be stable and cheap. However, the apparatus will still be comprised by the basic inventive idea as defined in the attached claims, even if other constructive materials are used and the flexibility of the apparatus is slightly lower than previously described.

We claim:
1. Bone aligning apparatus comprising,
a vertically oriented member having a lower end including means for attaching said member to a desired supporting structure and an upper end including a first cross piece;
an upper beam slidingly attached to said member at said first cross piece and extending longitudinally relative to said member, said upper beam including a first roller at one end and a second roller at the other end;
a second cross piece slidingly attached to said member and spaced from said first cross piece;
a lower beam slidingly attached to said member at said second cross piece and extending longitudinally relative to said member, said lower beam including a crank device at one end and a holder slidingly attached to the other end;
a rope one end of which is operatively attached to said crank device, said rope being supported by said first and second rollers, the other end of said rope extending from said second roller towards said other end of said lower beam;
a limb retaining means attached to said holder; and,
a repositioning disc attached to said other end of said rope and including means adapted to hold the extreme portions of a limb in a physiologically cor- rect position whereby actuation of said crank device causes said rope to pull said repositioning disc away from said retaining means.

2. The bone aligning device of claim 1 wherein a pulling force meter subdivides said rope for indicating the amount of force being exerted when actuation of said crank device causes said rope to pull said repositioning disc away from said retaining means.

3. The bone aligning device of claim 1 wherein said crank device is swingably mounted to said lower beam.

4. The bone aligning device of claim 2, wherein said crank device is swingable mounted to said lower beam.

5. The bone aligning device of claim 1 including a spring, one end of which is attached to said holder and the other end of which is attached to said limb retaining means.

6. Bone aligning apparatus comprising,
a vertically oriented member having a lower end including means for attaching said member to a desired supporting structure and an upper end including a first cross piece;
an upper beam slidingly attached to said member at said first cross piece and extending longitudinally relative to said member, said upper beam including a first roller at one end and a second roller at the other end;
a second cross piece slidingly attached to said member and spaced from said first cross piece;
a lower beam slidingly attached to said member at said second cross piece and extending longitudinally relative said member, said lower beam including a crank device swingably mounted at one end and a holder slidingly attached to the other end;
a first rope one end of which is operatively attached to said crank device and the second end of which is operatively attached to one side of a pulling force meter, and a second rope, one end of which is operatively attached to another side of said pulling force meter and the second end of which is supported by said first and second rollers, said second end of said second rope ultimately extending from said second roller towards said other end of said lower beam;
a spring, one end of which is attached to said holder and the other end of which is attached to a limb retaining means; and,
a repositioning disc attached to said other end of said rope and including means adapted to hold the extreme portions of a limb in a physiologically correct position whereby actuation of said crank device causes said rope to pull said repositioning disc away from said retaining means.

* * * * *